ized Patent [19]

Nodelman et al.

[11] Patent Number: 4,859,791

[45] Date of Patent: Aug. 22, 1989

[54] HIGH SOLIDS POLYESTER POLYOLS

[75] Inventors: Neil H. Nodelman, Pittsburgh; Robert G. Kelso, Wexford, both of Pa.

[73] Assignee: Mobay Corporation, Pittsburgh, Pa.

[21] Appl. No.: 21,106

[22] Filed: Mar. 3, 1987

[51] Int. Cl.[4] .................. C07C 69/80; C07C 69/75
[52] U.S. Cl. ............................... 560/91; 521/81; 525/440; 560/90; 560/127
[58] Field of Search .................. 560/90, 91, 127

[56] References Cited

U.S. PATENT DOCUMENTS 3,966,683  6/1976  Merten et al. ............... 548/308 X
4,439,591  3/1984  Buschhaus et al. ............. 528/73

*Primary Examiner*—Werren B. Lone
*Assistant Examiner*—Vera C. Clarke
*Attorney, Agent, or Firm*—Gene Harsh; Joseph C. Gil; Thomas W. Roy

[57] ABSTRACT

The present invention is directed to a polyester polyol having a molecular weight between about 850 and 2000, a functionality of about 5 to 9 and an OH number of about 200 to 350, based on 100% solids, which is prepared by reacting (a) an acid component based on at least one polyfunctional cycloaliphatic or aromatic carboxylic acid, anhydride or ester and optionally up to about 50 percent by weight of at least one acyclic, polyfunctional carboxylic acid and (b) a hydroxyl component containing at least a portion of at least one polyol having a functionality of at least 3.

The present invention is also directed to a process for preparing these polyester polyols by reacting the above components and is further directed to the use of these polyester polyols in combination with organic polyisocyanates for the production of polyurethanes, particularly polyurethane coatings.

4 Claims, No Drawings

HIGH SOLIDS POLYESTER POLYOLS

BACKGROUND OF THE INVENTION

1. Field of the Invention

The present invention is directed to polyester polyols which have a low viscosity so that they may be formulated at high solids contents for use in the preparation of polyurethanes, particularly polyurethane coatings.

2. Description of the Prior Art

It is known to use polyester polyols for the production of hard, flexible polyurethane coatings having good acid and chemical resistance, gloss retention and abrasion resistance as well as light stability when (cyclo)aliphatic polyisocyanates are used as co-reactants. In order to obtain these properties highly branched polyester polyols are reacted with the organic polyisocyanates. However, due to the high degree of branching, the polyester polyols have a high viscosity and considerable amounts of solvent must be used to reduce the viscosity of the polyester polyols to an acceptable level, especially if the coatings are applied in a spray application. Because the use of large amounts of solvent may create environmental difficulties, particularly in a spray application, there is a need for polyester polyols which have a lower viscosity so that they may be formulated with less solvent than with previously known polyester polyols. It is also important to maintain the coatings properties obtained from the highly branched polyester polyols.

Accordingly, it is an object of the present invention to provide low viscosity polyester polyols which may be formulated at high solids contents than previously known polyester polyols such that the polyester polyols may be used in spray applications. It is also an object of the present invention to provide polyester polyols which may be used to produce polyurethane coatings which maintain the level of coatings properties obtained from the previously known polyester polyols, i.e. good acid and chemical resistance, gloss retention, abrasion resistance and light stability. Surprisingly, these objects may be achieved by using the polyester polyols of the present invention set forth hereinafter.

SUMMARY OF THE INVENTION

The present invention is directed to a polyester polyol having a molecular weight between about 850 and 2000, a functionality of about 5 to 9 and an OH number of about 200 to 350, based on 100% solids, which is prepared by reacting (a) an acid component based on at least one polyfunctional cycloaliphatic or aromatic carboxylic acid, anhydride or ester and optionally up to about 50 percent by weight of at least one acyclic, polyfunctional carboxylic acid and (b) a hydroxyl component containing at least a portion of at least one polyol having a functionality of at least 3.

The present invention is also directed to a process for preparing these polyester polyols by reacting the above components and is further directed to the use of these polyester polyols in combination with organic polyisocyanates for the production of polyurethanes, particularly polyurethane coatings.

DETAILED DESCRIPTION OF THE INVENTION

It was very unexpected that the polyester polyols according to the invention which have a lower viscosity and functionality than previously known polyester polyols could be used for producing polyurethane coatings which have properties which are not substantially different from coatings prepared with the higher viscosity and functionality polyester polyols known in the industry. This is especially surprising with regard to the solvent resistance which is dependent upon the crosslink density which in turn is directly related to the functionality or amount of branching of the polyester polyol.

The polyester polyols generally have a molecular weight of about 850 to 2000, preferably about 1000 to 1700; a functionality of about 5 to 9, preferably about 6 to 8; and an OH number of about 200 to 350, preferably about 230 to 330 and most preferably about 250 to 300, based on 100% solids. The polyester polyols may be prepared by reacting polybasic, generally dibasic carboxylic acids with polyols wherein at least a portion of the polyols have a functionality of at least 3. In the preparation of the polyester polyols it is possible to use the corresponding polycarboxylic acid anhydrides or polycarboxylic acid esters of lower alcohols instead of the free polycarboxylic acids.

Suitable aromatic or cycloaliphatic polycarboxylic acids for preparing the polyester polyols include phthalic acid, isophthalic acid, terephthalic acid, phthalic acid anhydride, tetrahydrophthalic acid anhydride, hexahydrophthalic acid anhydride, tetrachlorophthalic acid anhydride, endomethylene tetrahydrophthalic acid anhydride, tetrahydroisophthalic acid, hexahydroisophthalic acid, tetrahydrophthalic acid, hexahydrophthalic acid, tetrahydroterephthalic acid, hexahydroterephthalic acid, dimethylterephthalate and bis-glycolterephthalate.

In addition to the aromic or cycloaliphatic polycarboxylic acids, which should be used in a quantity of at least about 50 percent by weight, preferably at least about 60 percent by weight, of the acid component of the polyester, it is also possible to use acyclic polycarboxylic acids such as succinic acid, succinic acid anhydride, adipic acid, suberic acid, azelaic acid, sebacic acid, glutaric acid, malonic acid and unsaturated acids such as maleic acid, maleic acid anhydride or fumaric acid. The previously described polycarboxylic acids may be unsaturated or they may be substituted, e.g. by halogen atoms. In addition to the dicarboxylic acids previously described, it is also possible to use polyfunctional carboxylic acids such as trimellitic acid or trimellitic acid anhydride in order to provide branching in the polyester polyol. However, it is preferred to introduce branching through the polyol component used to prepare the polyester polyol. Further, it is also possible to use monocarboxylic acids such as 2-ethylhexanoic acid to control the functionality.

The low molecular weight polyol reaction partner for use in preparing the polyester polyols include the low molecular weight chain extenders known from polyurethane chemistry. It is preferred to introduce the branching into the polyester polyols by using low molecular weight polyols having a functionality of at least 3 as at least a portion of the hydroxyl component. Suitable polyfunctional chain extenders include trimethylolpropane-(1,1,1), glycerol, hexanetriol-(1,2,6), butanetriol-(1,2,4), trimethylolethane-(1,1,1), pentaerythritol, mannitol, sorbitol, methyl glycoside, sucrose, and 1,1,2- or 1,1,1-tris-(hydroxyphenyl)-ethane.

Low molecular weight diols and monoalcohols may be blended with the higher functional polyols in order to achieve the desired functionality. Suitable diols include ethylene glycol, propylene glycol-(1,2) and -(1,3), butylene glycol-(1,4), -(1,3), and -(2,3), hexanediol-(1,6), octanediol-(1,8), neopentyl glycol, cyclohexanedimethanol (1,4-bis-hydroxymethylcyclohexane) and 2-methyl-1,3-propanediol. As in the case of monocarboxylic acids, it is also possible to use monoalcohols such as methanol, ethanol, propanol, butanol, 2-ethylhexanol, etc., in minor quantitites to control the functionality.

The molar proportions of polyols and polycarboxylic acids employed are such that there is an excess of hydroxyl groups over the number of carboxylic acid groups.

The functionality ($f_{OH}$) may be determined by the following formula $$f_{OH} = \frac{\Sigma \text{Equiv}_{OH} - \Sigma \text{Equiv}_{acid}}{\Sigma \text{Moles}_{OH} + \Sigma \text{Moles}_{acid} - \Sigma \text{Equiv}_{acid}}$$

For example, if two moles of a glycol (4 OH equivalents), 2 moles of a triol (6 OH equivalents) and three moles of a diacid (6 acid equivalents) are reacted to form a polyester polyol, then the theoretical average functionality is four. When monofunctional acid is used to reduce the functionality, the above formula may still be used. Thus, if one mole of a monocarboxylic acid (1 acid equivalent) is added to the above ingredients, the theoretical average functionality is three. By varying the amounts and functionalities of the individual components, polyester polyols with virtually any theoretical average functionality may be obtained.

The reaction between the glycol and the acid is carried out under normal esterification conditions well known and described in the prior art; see for example Polyurethanes: Chemistry and Technology, Part I, pages 45–46, 1962, J. H. Saunders and K. C. Frisch, John Wiley & Sons, New York, N.Y. Illustratively, the esterification is conducted in the absence of solvent under a flow of nitrogen and at temperatures of about 150° C. to 250° C., preferably about 190° C. to 225° C. for a period of about 4 to 40 hours, preferably about 6 to 24 hours. The reaction is terminated when the acid number of the product is less than about 4, preferably less than about 2. Water of condensation which is formed as a by-product during the reaction may be removed by conducting the reaction under vacuum conditions.

While catalysts are not necessary, they may be employed to shorten the esterification period. Suitable catalysts include p-toluene-sulfonic acid, magnesium oxide, calcium oxide, antimony oxide, zinc oxide, lead oxide, magnesium acetate, calcium acetate, zinc acetate, lead acetate, sodium acetate, potassium acetate, sodium 2-ethylhexanoate, potassium 2-ethylhexanoate, various organic amines, sodium methoxide, potassium methoxide, sodium alkoxytitanates, tetraalkyl titanates, hydrated monobutyl tin oxide, stannous oxalate, stannous chloride dihydrate and the like.

In order to prepare the two component polyurethane coating compositions, the polyester polyols are blended and reacted with suitable organic polyisocyanates known from polyurethane chemistry. The organic polyisocyanate may be monomeric in nature or polyisocyanate adducts prepared from monomeric polyisocyanates, preferably diisocyanates, and containing biuret, allophanate, urea, urethane or carbodiimide groups or isocyanurate rings. Suitable isocyanates and methods for preparing the polyisocyanate adducts are set forth in U.S. Pat. No. 4,439,593 herein incorporated by reference. The polyisocyanate adducts are preferably used to prepare the coatings especially when the coatings are applied by spray applications, due to their lower vapor pressure.

Preferred polyisocyanate adducts are biuret group-containing polyisocyanates based on 1,6-diisocyanatohexane and polyisocyanate adducts containing isocyanurate groups and based on 2,4-diisocyanatotoluene and/or 2,6-diisocyanatotoluene, 1,6-diisocyanatohexane, isophorone diisocyanate and mixtures of these diisocyanates. Also preferred are polyisocyanate adducts containing urethane groups and based on trimethylol propane and 2,4-diisocyanatotoluene and/or 2,6-diisocyanatotoluene, 1,6-diisocyanatohexane, isophorone diisocyanate and mixtures of the diisocyanates. The most preferred polyisocyanate adducts are the biuret group-containing polyisocyanates based on 1,6-diisocyanatohexane, polyisocyanate adducts containing isocyanurate groups and based on 1,6-diisocyanatohexane and polyisocyanate adducts containing urethane groups based on trimethylolpropane and isomeric mixtures of diisocyanatotoluene. The former two most preferred polyisocyanate adducts are especially preferred when resistance to yellowing under the effect of ultraviolet light is required. Mixtures may also be used, especially mixtures of the biuret group-containing polyisocyanates based on 1,6-diisocyanatohexane and the polyisocyanate adducts containing isocyanurate groups and based on 1,6-diisocyanatohexane as set forth in copending application, U.S. Ser. No. 738,909, filed Dec. 8, 1986.

In addition to the polyester polyols and the polyisocyanates, the coating composition may also contain solvents, catalysts, pigments, dyes, levelling agents, and the like which are well known in the field of polyurethane chemistry.

Even though the compositions according to the present invention require less solvent than those of the prior art to achieve a suitable processing viscosity, especially when used in spray applications, solvents may be added to the systems to further reduce their viscosity. Suitable solvents include the known polyurethane solvents such as toluene, xylene, butylacetate, ethylacetate, ethylene glycol monoethyl ether acetate, ethylene glycol monomethyl ether acetate, ethylene glycol monobutyl ether acetate, ethylene glycol monohexyl ether acetate, propylene glycol monomethyl ether acetate, diethylene glycol monoethyl ether acetate, diethlyene glycol monobutyl ether acetate, methyl ethyl ketone, methyl isobutyl ketone, methyl amyl ketone, hydrocarbon solvents such as hexane and heptane, aromatic solvents and also mixtures of these solvents.

Suitable polyurethane catalysts include those known in polyurethane chemistry such as tertiary amines, quaternary ammonium hydroxides, alkali metal hydroxides, alkali metal alcoholates, alkali metal phenolates and, in particular, organic tin compounds. The catalysts are generally used in a quantity of about 0.001 to 10 percent by weight, based on the quantity of polyesters used according to the invention.

Suitable pigments include the known inorganic and organic pigments and dyes, particularly inorganic pigments such as iron oxide, carbon black and titanium dioxide.

The coatings according to the invention may be applied by any of the known, conventional methods such as roller, brush or immersion, especially spray gun or airless spray gun.

The invention is further illustrated but is not intended to be limited by the following examples in which all parts and percentages are by weight unless otherwise specified.

EXAMPLES

The following components were used in the examples:

Polyisocyanate A—an isocyanurate group-containing polyisocyanate having an equivalent weight of 216, prepared by trimerizing hexamethylene diisocyanate and present at 90% solids in a mixture of equal parts n-butyl acetate and solvent naphtha 100 (available as Desmodur N 3390 from Mobay Corporation).

Polyisocyanate B—a biuret group-containing polyisocyanate based on hexamethylene diisocyanate and having an equivalent weight of 183 (available as Desmodur N 3200 from Mobay Corporation).

Polyisocyanate C—a urethane group-containing polyisocyanate prepared from toluene diisocyanate and trimethylol propane (available as Mondur CB-75 from Mobay Corporation).

The following polyester polyols were prepared by charging the reactants to a closed reaction vessel while maintaining a nitrogen blanket. The reactants were heated to 210° C. and reacted at atmospheric pressure until about 80% of the theoretical water has been collected. At that time the pressure was reduced to a level of about 10 to 15 mm Hg. The reaction was maintained under these conditions until the acid number was reduced to a value of less than 2 mg KOH/g at 100% solids. After completion of the reaction, the reactants were cooled and during this step the solvent was added. All of the equivalent weights and OH numbers set forth are based on 100% solids.

Polyol A—a polyester polyol present as a 75% solids solution in propylene glycol monomethyl ether acetate, having an equivalent weight of about 195, an OH number of about 288 and a functionality of about 6.4, and prepared from
47.0 parts 2-ethylhexanoic acid
409.8 parts trimethylol propane
239.6 parts phthalic acid anhydride and
119.8 parts adipic acid.

Polyol B—a polyester polyol present as an 80% solids solution in propylene glycol monomethyl ether acetate, having an equivalent weight of about 200, an OH number of about 280 and a functionality of about 6.4, and prepared from the same reactants and amounts as Polyol A.

Polyol C—a commercially available polyester polyol present as a 65% solids solution in proplyene glycol monomethyl ether acetate, having an equivalent weight of about 215, an OH number of about 260 and a functionality of about 12-12.5, and prepared from trimethylol propane and phthalic acid anhydride.

Polyol D—a commercially available polyester polyol present as a 65% solids solution in propylene glycol monomethyl ether acetate, having an equivalent weight of about 215, an OH number of about 260 and a functionality of about 12-12.5, and prepared from trimethylol propane, hexahydrophthalic acid anhydride and phthalic acid anhydride.

Additive A—a 33% solution in a 1:1 mixture of methyl ethyl ketone and propylene glycol monomethyl ether acetate of a cellulose acetate/butyrate flow aid (available as CAB-551-0.1 sec from Eastman Chemical).

Additive B—a 10% solution in propylene glycol monomethyl ether acetate of a fluorocarbon surfactant (available as FC-430 from 3M Company).

Additive C—a 50% solution in a proprietary solvent of a wetting and suspending agent based on the salt of a long chain polyaminoamide and a high molecular weight acid ester (available as Antiterra U from Byk Chemie).

Additive D—a hindered amine light stabilizer (available as Tinuvin 292 from Ciba-Geigy).

Additive E—a benzotriazole light stabilizer (available as Tinuvin 1130 from Ciba-Geigy).

Catalyst A—a 1% solution in propylene glycol monomethyl ether acetate of dibutyl tin dilaurate (available as T-12 from Air Products and Chemicals).

Catalyst B—a 1% solution in a 1:1 mixture of propylene glycol monomethyl ether acetate and methyl ethyl ketone of dibutyl tin dilaurate (available as T-12 from Air Products and Chemicals.

Solvent Blend A—a blend of 40 parts propylene glycol monomethyl ether acetate, 10 parts n-butyl acetate, 40 parts methyl ethyl ketone and 10 parts xylene.

Solvent Blend B—a blend of equal parts methyl amyl ketone, methyl isobutyl ketone and methyl n-propyl ketone.

EXAMPLE 1

A pigmented polyol composition was prepared by mixing the following:
1200.0 parts of Polyol A
1415.3 parts TiO$_2$
105.0 parts Additive A
16.0 parts Additive B
9.4 parts Additive C
627.6 parts Solvent Blend A.

153.8 parts of this polyol composition were mixed with 37.5 parts of Polyisocyanate A, 10.4 parts of Polyisocyanate B (NCO equivalent ratio 75/25), 15.2 parts of Solvent Blend A and 0.6 parts of Catalyst A. This coating composition was sprayed onto steel panels using a Binks Model 18 conventional air gun with a 66SF tip at 40 psi. An excellent coating was obtained which had good gloss and did not suffer from pigment flocculation.

EXAMPLE 2

A pigmented polyol composition was prepared from the following:
1129.2 parts Polyol A
1280.4 parts TiO$_2$
98.8 parts Additive A
15.2 parts Additive B
12.8 parts Additive C
25.6 parts Additive D
8.0 parts Additive E 34.0 parts Catalyst B
900.0 parts Solvent Blend A.

150 parts of the pigmented polyol composition were mixed with 22.1 parts of Polyisocyanate A and 18.4 parts of Polyisocyanate B (NCO equivalent ratio 50/50). The coating composition was applied to steel panels in the manner of Example 1. An excellent coating was obtained which had good gloss and did not suffer from pigment flocculation.

EXAMPLE 3

150 parts of the pigmented polyol composition of Example 2 were blended with a mixture of 33.1 parts of Polyisocyanate A and 9.2 parts of Polyisocyanate B (NCO equivalent ratio 75/25). The coated composition was applied to steel panels in the manner of Example 1. An excellent coating was obtained with good gloss which did not suffer from pigment flocculation.

EXAMPLE 4

A pigmented polyol composition was prepared by mixing the following:
265.0 parts of Polyol B
25.8 parts Additive A
4.1 parts Catalyst B
63.2 parts Solvent Blend B.

100 parts of this polyol composition were mixed with 53.7 parts of Polyisocyanate B to form a coating composition having a solids content of 75%.

The viscosity of the coating composition was measured using a number 4 Ford Cup at various solid contents obtained by diluting the composition with Solvent Blend B.
Viscosity at
75% solids = 5 minutes, 4 seconds
71% solids = 2 minutes, 55 seconds
65% solids = 1 minute, 12 seconds
61% total solids = 45 seconds A freshly prepared sample immediately diluted to 61% solids had a viscosity of 31 seconds.

Films prepared from the coating composition had the following properties:
Pencil hardness—2H
Methyl ethyl ketone (MEK) double rubs—200
Gardner impact (direct/reverse)—160/160 in-lbs.

EXAMPLE 5 (Comparison)

A polyol composition was prepared by mixing the following:
362.2 parts Polyol D,
25.8 parts Additive A,
4.1 parts Catalyst B
2.0 parts Solvent Blend B.

100 parts of this polyol composition were mixed with 53.7 parts of Polyisocyanate B to form a coating composition having a solids content of 75%. The viscosity of the coating composition was measured using a number 4 Ford Cup at various solids contents obtained by diluting the coating composition with Solvent Blend B.
Viscosity at
75% solids = too viscous to measure
65% solids = 2 minutes, 33 seconds
55% solids = 32 seconds Films prepared from the coating composition were very hazy and had the following properties
Pencil hardness = 3-4H
MEK double rubs = 200
Gardner impact = 40/20 in-lbs.

EXAMPLE 6

A polyol composition was prepared by mixing the following:
265 parts Polyol B
26.4 parts Additive A
4.1 parts Catalyst B
44.5 parts Solvent Blend B.

100 parts of this polyol composition were mixed with 67.6 parts of Polyisocyanate A to form a coating composition having a solids content of 75%. The viscosity of the coating composition was measured using a number 4 Ford Cup at various solids contents obtained by diluting the coating composition with Solvent Blend B.
Viscosity at
75% solids = 4 minutes, 58 seconds
71% solids = 2 minutes, 29 seconds
65% solids = 56 seconds
61% solids = 35 seconds The viscosity at 61% solids of a freshly made sample was 28 seconds.

Films prepared from the coating composition had the following properties:
Pencil hardness = 2H
MEK double rubs = 200
Gardner Impact = 120/100 in-lbs.

EXAMPLE 7 (Comparison)

A polyol composition was prepared by mixing the following:
326.2 parts Polyol D
26.4 parts Additive A
4.1 parts Catalyst B.

100 parts of this polyol composition were mixed with 64.4 parts of Polyisocyanate A to form a coating composition having a solids content of 73%. The viscosity of the coating composition was measured using a number 4 Ford Cup at various solids contents obtained by diluting the coating composition with Solvent Blend B.
Viscosity at
73% solids = too viscous to measure
65% solids = 2 minutes, 19 seconds
55% solids = 28 seconds.

Films prepared from the coating composition were hazy and had the following properties:
Pencil hardness = 3-4H
MEK double rubs = 200
Gardner impact = 40/20 in-lbs.

EXAMPLE 8

A polyol composition was prepared by mixing the following:
611.8 parts Polyol A
61.2 parts Additive A
12.2 parts Catalyst B.

100 parts of this polyol composition were mixed with 67.1 parts of Polyisocyanate B to form a coating composition having a solids content of 82%. The viscosity of the coating composition was measured using a number 4 Ford Cup at various solvent contents obtained by diluting the coating composition with Solvent Blend B.
Viscosity at
75% solids = greater than 5 minutes
65% solids = 1 minute, 3 seconds
55% solids = 22 seconds

EXAMPLE 9 (Comparison)

A polyol composition was prepared by mixing the following:
648 parts Polyol C
64.8 parts Additive A
13 parts Catalyst B.

100 parts of this coating composition were mixed with 55.5 parts of Polyisocyanate B to form a coating composition having a solids content of 75%. The viscosity of the coating composition was measured using a number 4 Ford Cup at various solids contents obtained by diluting the coating composition with Solvent Blend B.

Viscosity at
74% solids = too viscous to measure
65% solids = 3 minutes, 42 seconds
55% solids = 44 seconds.

EXAMPLE 10

100 parts of the polyol composition set forth in Example 8 were mixed with 79.1 parts of Polyisocyanate A to form a coating composition having a solids content of 78.7%. The viscosity of the coating composition was measured using a number 4 Ford Cup at various solids contents obtained by diluting the coating composition with Solvent Blend B.

Viscosity at
75% solids = 4 minutes
65% solids = 47.6 seconds
55% solids = 19 seconds.

EXAMPLE 11 (Comparison)

100 parts of the polyol composition set forth in Example 9 were mixed with 65.8 parts of Polyisocyanate A to form a coating composition having a solids content of 72.4%. The viscosity of the coating composition was measured using a number 4 Ford Cup at various solids contents obtained by diluting the coating composition with Solvent Blend B.

Viscosity at
72.4% solids = too viscous to measure
65% solids = 3 minutes, 20 seconds
55% solids = 31.4 seconds.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyester polyol having a molecular weight between about 850 and 2000, a functionality of about 5 to 9 and an OH number of about 200 to 350, based on 100% solids, which is prepared by reacting a mixture comprising
   (a) an active component based on at least one polyfunctional cycloaliphatic or aromatic carboxylic acid, anhydride or ester and optionally up to about 50% by weight of at least one acyclic, polyfunctional carboxylic acid and
   (b) a hydroxyl component containing at least a portion of at least one polyol having a functionality of at least 3.

2. The polyester polyol of Claim 1 wherein the acid component comprises phthalic acid anhydride.

3. The polyester polyol of Claim 1 wherein the hydroxyl group comprises trimethylol propane.

4. The polyester polyol of Claim 2 wherein the hydroxyl group comprises trimethylol propane.

* * * * *